(12) United States Patent
Niu et al.

(10) Patent No.: US 8,073,099 B2
(45) Date of Patent: Dec. 6, 2011

(54) DIFFERENTIAL INTERFERENCE PHASE CONTRAST X-RAY IMAGING SYSTEM

(75) Inventors: Han-Ben Niu, Shenzhen (CN); Jin-Chuan Guo, Shenzhen (CN); Xin Liu, Shenzhen (CN)

(73) Assignee: Shenzhen University, Shenzhen, Guangdong (CN)

( * ) Notice: Subject to any disclaimer, the term of this patent is extended or adjusted under 35 U.S.C. 154(b) by 155 days.

(21) Appl. No.: 12/426,991

(22) Filed: Apr. 21, 2009

(65) Prior Publication Data

US 2010/0091947 A1      Apr. 15, 2010

(30) Foreign Application Priority Data

Oct. 10, 2008   (CN) .......................... 2008 1 0216469

(51) Int. Cl.
*G01N 23/083* (2006.01)
(52) U.S. Cl. ........................................... 378/36; 378/62
(58) Field of Classification Search .................. 378/19, 378/36, 62, 70, 82, 86, 98.8; 250/370.09, 250/580, 591, 590
See application file for complete search history.

(56) References Cited

U.S. PATENT DOCUMENTS

| | | | | |
|---|---|---|---|---|
| 5,354,982 A * | 10/1994 | Nelson et al. | ........... | 250/214 LA |
| 5,812,629 A * | 9/1998 | Clauser | ........................... | 378/62 |
| 6,078,643 A * | 6/2000 | Vogelsong et al. | ........... | 378/98.2 |
| 6,326,625 B1 * | 12/2001 | Zur | .......................... | 250/370.09 |
| 6,552,356 B2 * | 4/2003 | Imai | .............................. | 250/580 |
| 6,633,627 B2 * | 10/2003 | Horiuchi | ....................... | 378/156 |
| 7,433,444 B2 * | 10/2008 | Baumann et al. | ............... | 378/62 |
| 7,440,542 B2 * | 10/2008 | Baumann et al. | ............... | 378/45 |
| 7,453,981 B2 * | 11/2008 | Baumann et al. | ............... | 378/62 |
| 7,486,770 B2 * | 2/2009 | Baumann et al. | ............... | 378/62 |
| 7,492,871 B2 * | 2/2009 | Popescu et al. | ............... | 378/145 |
| 7,522,698 B2 * | 4/2009 | Popescu et al. | ................. | 378/19 |
| 7,522,708 B2 * | 4/2009 | Heismann et al. | ............ | 378/145 |
| 7,535,986 B2 * | 5/2009 | Hempel | ........................... | 378/4 |

(Continued)

FOREIGN PATENT DOCUMENTS

CN       200610062487.1        2/2007

(Continued)

OTHER PUBLICATIONS

Engelhardt, et. al, High-Resolution Differential Phase Contrast Imaging Using Microfocus X-ray Sources, International Sumposium on Digital industrial Radiology, 2007, France.

*Primary Examiner* — Allen C. Ho
(74) *Attorney, Agent, or Firm* — Harris Shelton Hanover Walsh

(57) ABSTRACT

A differential phase-contrast X-ray imaging system is provided. Along the direction of X-ray propagation, the basic components are X-ray tube, filter, object platform, X-ray phase grating, and X-ray detector. The system provides: 1) X-ray beam from parallel-arranged source array with good coherence, high energy, and wider angles of divergence with 30-50 degree. 2) The novel X-ray detector adopted in present invention plays dual roles of conventional analyzer grating and conventional detector. The basic structure of the detector includes a set of parallel-arranged linear array X-ray scintillator screens, optical coupling system, an area array detector or parallel-arranged linear array X-ray photoconductive detector. In this case, relative parameters for scintillator screens or photoconductive detector correspond to phase grating and parallel-arranged line source array, which can provide the coherent X-rays with high energy.

2 Claims, 4 Drawing Sheets

U.S. PATENT DOCUMENTS

| | | | |
|---|---|---|---|
| 7,564,941 B2 * | 7/2009 | Baumann et al. | 378/19 |
| 7,639,786 B2 * | 12/2009 | Baumann et al. | 378/145 |
| 7,646,843 B2 * | 1/2010 | Popescu et al. | 378/5 |
| 7,746,981 B2 * | 6/2010 | Takahashi et al. | 378/98.8 |
| 7,817,777 B2 * | 10/2010 | Baumann et al. | 378/62 |
| 7,889,838 B2 * | 2/2011 | David et al. | 378/36 |
| 7,924,973 B2 * | 4/2011 | Kottler et al. | 378/36 |

FOREIGN PATENT DOCUMENTS

| | | | |
|---|---|---|---|
| WO | WO2007/074029 A1 * | 7/2007 | |

* cited by examiner

DIFFERENTIAL INTERFERENCE PHASE CONTRAST X-RAY IMAGING SYSTEM

RELATED APPLICATION

This application claims the benefit of Peoples' Republic of China application Serial No. 200810216469.3 filed on Oct. 10, 2008, hereby specifically incorporated by reference in its entirety.

FIELD OF THE INVENTION

This invention provides a differential interference phase-contrast X-ray imaging system.

DESCRIPTION OF RELATED ART

Noninvasive imaging plays an important role and has been widely applied in many fields like medicine, life science, material science, industrial application, and security inspection etc. X-ray imaging is one of the most important methods for noninvasive imaging. The contrast of conventional X-ray radiography based upon the attenuation of X-ray is obtained through difference in the absorption cross-section of the constituents of the object. But a weakly absorbing object consisting of light elements which does not absorb X-ray so much is too transparent for X-ray to create a sufficient contrast detected by X-ray detector. Especially in the fields of medicine and biology, most of tissues, such as blood vessel, breast hollow organ and tumor, are weakly absorbing material made of light elements. The technique yields excellent results where highly absorbing structures containing heavy elements, such as bones. However, with respect to those soft tissues, the X-ray absorbing contrast is relatively poor.

X-ray phase-contrast imaging is a method to records the contrast caused by phase shift of object. The phase factor causing phase shift is three orders of magnitude greater than the absorption factor causing intensity attenuation for light elements. Therefore, X-ray phase-contrast imaging is much more sensitive to soft tissues than attenuation-based imaging. Theoretically, phase-sensitive techniques are able to differentiate boundaries of tissue, whose density distribution is 0.0003-0.002 $g/cm^3$, with spatial resolution of smaller than 1 μm. As present the best method for soft tissue in medical examination, Magnetic Resonance Imaging can detect a density distribution of 0.01 $g/cm^3$, whose spatial resolution is only 1-2 mm. Furthermore, the people imaged with X-ray benefit from not only the reduction of the applied X-ray dose, because of image of phase shift instead of absorbing image, but also sufficient contrast and higher spatial resolution.

When considering X-ray phase-contrast imaging system, An X-ray source with good coherence and higher radiant flux is necessary. Synchrotron radiation source can meet the requirement to some extent, and most experiments and investigations of phase-contrast image are performed on synchrotron sources. Nevertheless, synchrotron radiation source is too large and too expensive in most practical applications. Moreover, the conventional synchrotron radiation source cannot provide 40-70 keV photon energy that is necessary to generate satisfying contrast for medical applications.

X-ray tube based phase-contrast methods are still in stages of research and early development. Two technologies based on X-ray tube, which are in-line phase-contrast imaging that uses a micro-focus X-ray tube as source and differential interference phase-contrast imaging system consisting of two gratings, respectively, are developed. It is usually difficult or even impossible to apply the micro-focus X-ray tube as source in hospitals or any real time examination facility because it cannot provide sufficient radiant flux due to some critical limitations, like difficulty in heat dissipation. Another technique under development is differential interference phase-contrast imaging that can adopt the conventional low luminance X-ray tube as emitter. In order to provide the one-dimensional spatial coherence, an X-ray absorption grating must be set close the X-ray tube. As an analyzer grating, second absorption grating downstream of the phase grating is adopt to reduce the requirement of spatial resolution for X-ray detector. Limited by state of the art of micro-fabrication, the absorption grating cannot be too thick, and the corresponding X-ray photon energy cannot be over 30-40 keV. All of these limitations make the differential interference phase-contrast imaging unfeasible in hospitals.

Therefore, before implementing the differential interference X-ray phase-contrast imaging, a novel X-ray tube with good spatial coherence, sufficient radiant flux, and wide emission angle must be available. By bombarding the structure or non-structure anode with electron or ion beam, this new X-ray tube will be able to generate a set of parallel linear X-ray beams. With enough angles of divergence, the X-rays beams from the corresponding linear emitter can overlap each other, and contribute constructively to the image-formation process to fulfill requirement of imaging. A novel X-ray tube with advantages described above has been invented and produced in Shenzhen University. For detail information please refer to CN Patent application 200610062487.1.

How to realize the function of analyzer grating without such absorption grating in differential phase-contrast imaging system is another challenge. A novel X-ray detector has been proposed and developed to play the role of analyzer grating. This novel X-ray detector has one-dimensional periodic structure and the same periodicity of conventional analyzer grating. The difference is that the absorption part which is usually made of gold in an analyzer grating is now the segment which is insensitive to x-rays, and the transmission part of grating is now sensitive to x-rays in this detector. The former is called insensitive segment and the latter insensitive one, which are together form the basic repeated unit of periodic structure. The sensitive segment is composed of an array of pixels along the groove line in grating. The sum width of sensitive and insensitive segment is exactly same as the period of the pattern of interference X-ray beams. This novel X-ray detector plays dual roles of conventional analyzer grating and conventional detector.

In order to meet the requirement of one dimensional spatial coherence for low luminance X-ray tube, the last studies show that an aperture mask, typically an absorbing grating, should be set at the nearest location to the X-ray source. The origination of three grating lines of source mask, phase grating and analyzer grating should be parallel mutually. Although the phase-contrast image of sample can be obtain by the X-ray detector with high spatial resolution, the applications of two absorption grating, which work as generator of structure light and analyzer grating respectively, are significant limiting factors. With the increasing of X-ray photon energy, an insuperable difficulty in fabricating absorption grating occurs. Moreover, additional critical problems like view field, radiant flux, image distortion also occur. Therefore, although the principle of differential interference phase-contrast imaging based on low luminance X-ray source has been introduced several years ago, and the imaging system is able to generate excellent result on small experimental animals, the applications in medical diagnosis and other related fields are still technically challenged, or practically infeasible.

SUMMARY OF THE INVENTION

The present invention provides a novel differential interference phase-contrast X-ray imaging system containing a novel X-ray tube and X-ray detector.

Instead of two absorption grating that provide virtual X-ray radiation source with one dimensional spatial coherence and function of analyzer grating, a novel X-ray tube and detector is adopted to provide one dimension spatial coherence x-rays, with high radiant flux, high photon energy and wide emission angle, and a novel X-ray detector is used to record the phase contrast images, in the present invention. This novel X-ray detector has one-dimensional periodic structure. The size of the periodic structure is the same as that of a conventional analyzer grating. The difference is that the absorption part which is usually made of gold in an analyzer grating is now the segment which is insensitive to x-rays, and the transmission part of grating is now sensitive to x-rays in this detector. The former is called insensitive segment and the latter insensitive one, which are together form the basic repeated unit of periodic structure. The sensitive segment is composed of an array of pixels along the groove line in grating. The sum width of sensitive and insensitive segment is exactly same as the period of the pattern of interference X-ray beams. This novel X-ray detector plays dual roles of conventional analyzer grating and conventional detector. Moiré effect or phase-shift method is used in prevent invention to readout the phase contribution.

In accordance with the direction of X-ray propagation, the whole system is composed of X-ray tube, filter, object stage, phase grating, X-ray detector, and means to coordinate the orientations of the X-ray tube, phase grating line and X-ray detector by system administration software and computer.

The X-ray tube emits coherent, highly energetic X-ray beams, the focal spot of which has the shape of linear parallel-arranged with emission angle of 30-50 degrees.

The novel x-ray detector adopted plays dual roles of conventional analyzer grating and conventional detector. The basic structure of the detector includes a set of parallel-arranged line arrays of x-ray scintillator screens, transmission optical system, area array detector or photoconductive x-ray detector. The structure and size of the x-ray scintillator screen or the photoconductive x-ray detector are matched to the x-ray tube and the phase grating described above.

Two key innovations are proposed in present invention. The first innovation is the novel x-ray tube. The focal spot of the x-ray tube is a parallel line array, which dispenses with the absorption grating. This tube can work in the voltage range of 40-120 kV. By inserting an x-ray filter in the x-ray passage, the x-ray photon energy of the central wavelength of the x-ray beam emitted from the tube can be adjusted in the range of 20-100 keV, with a bandwidth of ±20%. Most importantly, this novel X-ray tube has several advantages like one dimension spatial coherence, high radiant flux, high photon energy and wide emission angle. Thus, invention of the tube provides a practicable x-ray source for the x-ray differential interference phase-contrast imaging system.

The second innovation is the x-ray detector. This novel x-ray detector has one-dimensional periodic structure that corresponds to the periodic parameters of the x-ray tube. The periodicity of the structure is equal to that of the analyzer grating in a standard differential interference x-ray imaging. The difference is that the absorption part which is usually made of gold in an analyzer grating is now the segment which is insensitive to x-rays, and the transmission part of grating is now sensitive to x-rays in this detector. The former is called insensitive segment and the latter insensitive one, which are together form the basic repeated unit of periodic structure. The sensitive segment is composed of an array of pixels along the groove line in grating. The sum width of sensitive and insensitive segment is exactly same as the period of interference pattern. This novel x-ray detector simultaneously plays dual roles of a conventional analyzer grating and a conventional detector. The application of this novel detector eliminates the insuperable disadvantages of a conventional x-ray detector where both very thick absorbing and analyzer gratings have to be involved. It is usually very difficult, or even impossible to produce very thick absorption grating and analyzer grating.

The present invention provides a novel x-ray detector with a function of an analyzer grating. This novel X-ray detector has a one-dimensional periodic structure. The direction of the periodic structure corresponds to the interference fringes direction of the x-ray phase grating; and the periodic pitch of the structure corresponds to the interference fringes pitch. In every loop cycle, half of the cycle is insensitive to X-ray; this is equivalent to adding an absorption grating with 100% absorbing ratio. Another half cycle of the periodic structure is the effective part for detection. The structure of the detector and the grating interference fringes generates Moiré fringes. Combining the detector and the analyzer grating to a single optoelectronic device not only reduces the number of optical compartments in the whole system, but diminishes the system complexity also. Moreover, the difficult task in making the absorption grating is avoided. The higher the X-ray photon energy, the harder to make the absorption grating. When an analyzer grating is used in medical imaging, the effective absorption thickness of the grating is usually over 300 μm, and the width of the interference pattern is only 1 μm, the aspect ratio is over 300; it is almost impossible to produce such an analyzer grating under present technology.

Based on the theory and method described above, the present invention provides a novel x-ray tube. The basic components of the x-ray tube include ionic/electronic emitter, grid electrode, electrostatic focusing electrode, and structure anode target. The structure anode is made from strip or block high Z elements metal like tungsten, molybdenum, and low Z elements like aluminum or beryllium arranged alternatively.

The strip or block high Z and low Z materials are reprocessed to meet the structure design, and then the high and low Z objects are aligned alternately. The transverse inclination angles are inversely arranged. The effective area of the structure anode that faces the electron or ionic beam is determined by the cross section area of the electron or ionic beam. This area is usually less than 1 mm$^2$.

The basic components of the secondary x-ray tube provided in the present invention include ionic/electronic emitter, focus system, electrostatic deflection system, and conventional anode without any structure. The electron or ionic beam is focused on the anode, and formed into a microbeam. The focused electron or ionic beams pass through the deflection system and scan on the anode, which emit x-rays with microfocal spot whose shape is a parallel line beam with width equal to the diameter of the microbeams of electron or ion in the placement.

The basic components of the third X-ray tube provided in the present invention include structured emitter, grid electrode, focus electrode, and conventional anode. The structured emitter uses electron or ionic source, and generates a set of parallel line array electron or ionic beam with a width of 0.005-0.1 mm.

The basic components of the fourth X-ray tube provided in present invention include electron or ionic emitter, multiple-slit accelerating electrode, focus electrode, and anode. The electron or ionic beams pass through the multiple-slit accelerating electrode, and are transformed to parallel electron or ionic beam. These parallel electron or ionic beams take a shape of multiple-slit diaphragm at the anode.

A grid electrode control circuit is provided in present invention to control the continuous or pulse regime of the electron or ion beam. By this control circuit, continuous or pulse radiation modes of x-ray can be alternately selected.

Present invention provides a novel x-ray detector. The detector is made of a scintillator screen and signal readout device. The base material of the scintillator screen is silicon with the micropore array structure generated by etching methods. The micropore array is oxidized or processed by vapor deposition to generate a reflective coating. The whole array is then filled with x-ray scintillator material to convert x-rays into fluorescent signals. The fluorescent signal can be read out by CCD or CMOS sensor through optical coupling element.

The second detector is a photoconductor x-ray detector. The geometry of this detector is similar as the scintillator screen in the first detector described above but with photoconductor material as the base material. X-rays are transformed to electric charge signals and can be readout by an electrical signal sensing device.

Present invention provides an X-ray differential interference phase-contrast imaging system. The system includes X-ray source, X-ray filter, object platform, X-ray phase grating and X-ray detector. The spectrum of X-ray tube in the present invention can be filtered to meet requirements of bandwidth and the central wavelength. The high of phase grating, which is set on an alignment jig that can be adjusted in 5 dimensions, corresponds to the central wavelength and bandwidth. The object is set between the X-ray source and the X-ray phase grating but adjacent to the phase grating. The X-ray detector is the detector of the present invention. The strike directions of the X-ray source, phase grating, and X-ray detector coordinate with each other one dimensionally to meet the requirement of imaging.

The second differential phase-contrast X-ray imaging system uses the alternative X-ray tube as the X-ray source; other components are same as the first differential phase-contrast X-ray imaging system.

The third differential phase-contrast X-ray imaging system uses the alternative X-ray detector of the present invention, other components are same as the first differential phase-contrast X-ray imaging system.

BRIEF DESCRIPTION OF THE DRAWINGS

FIG. 1 is a systemic schematic diagram of the differential phase-contrast X-ray imaging system. Elements in the figure are represented by the numbers as follows; 1-1 the X-ray tube with linear arrayed structure; 1-2 X-ray filter, 1-3 object platform, 1-4 X-ray phase grating, 1-5 detector with one dimensional periodicity.

FIG. 2 is a structure schematic diagram of a preferred embodiment of the X-ray detector composed with photon conductive material. Elements in the figure are represented by the numbers as follows; 2-1 glass base, 2-2 dielectric material, 2-3 the transparent electrode in the structure, 2-4 photoconductive material, 2-5 electrode. The T indicates the width of transparent electrode of 2-3.

FIG. 3 is the structure schematic diagram of partial scintillator screen in an alternative X-ray detector. X-ray fluorescent material is separated and forms a pixel unit array by the non-fluorescent material, the length and width of pixel unit are "a" and "b", respectively. In one-dimensional space, the period of the pixel unit array along X axis is P2, and the period along Y axis is C. The range of C is 0.5-10 μm.

FIG. 6 is the structure schematic diagram for an X-ray detector using techniques of optical fiber taper coupling, including 6-1 scintillator screen, 6-2 optical fiber taper, 6-3 array CCD or CMOS detector.

DETAILED DESCRIPTION OF THE PREFERRED EMBODIMENTS

Figure 1:
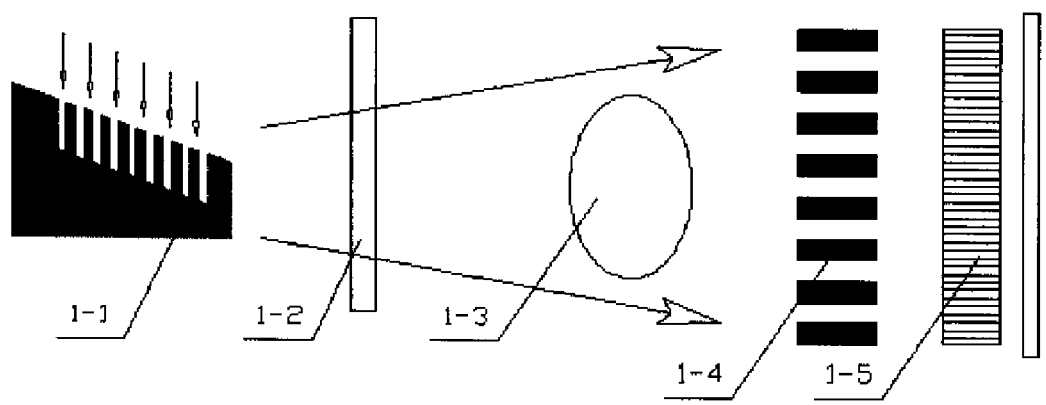
FIG. 1 is the system schematic diagram of present invention.
Figure 2:
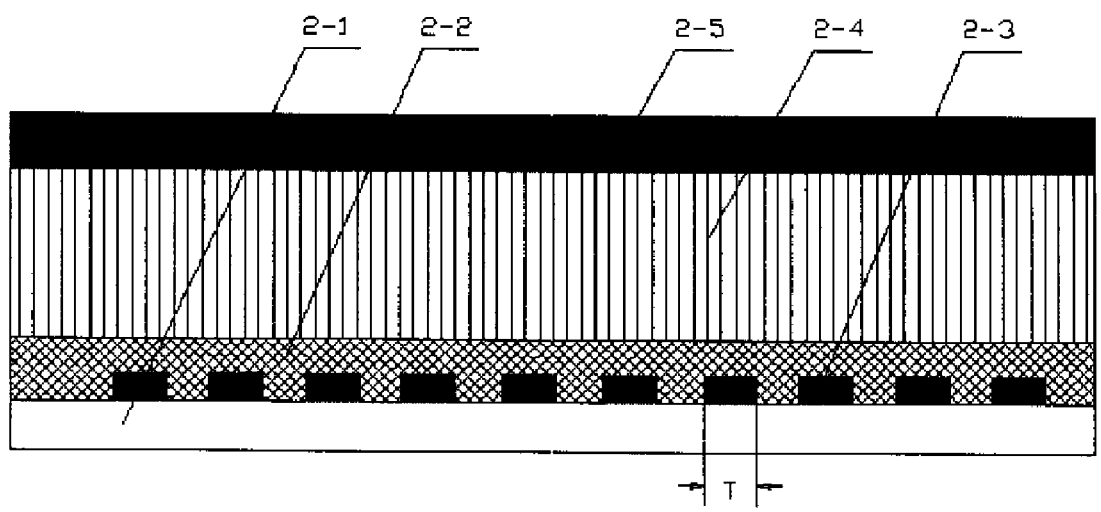
FIG. 2 is structure schematic diagram of a preferred embodiment of the interference fringes X-ray detector.
Figure 3:
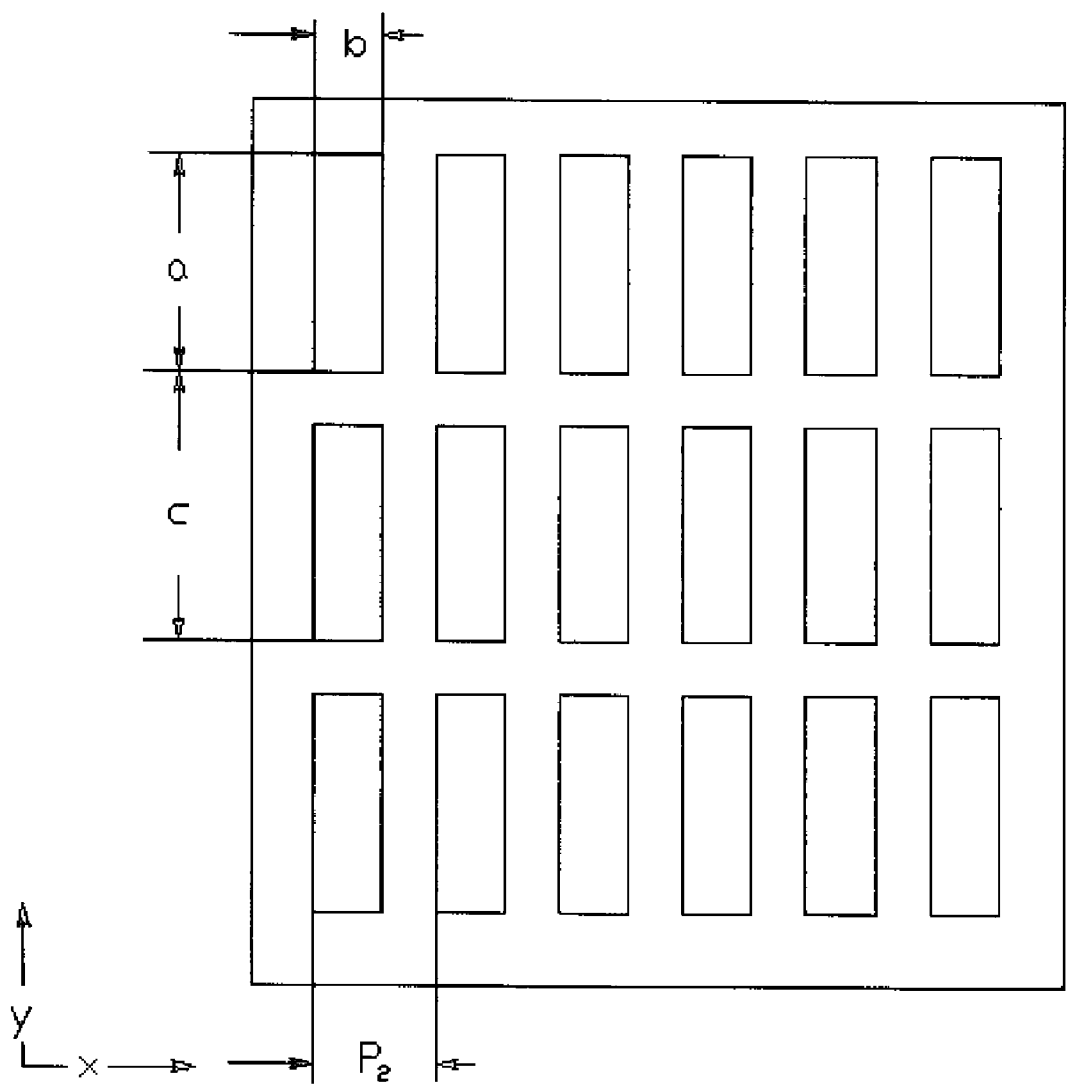
FIG. 3 is the structure vertical view of the partial scintillator screen in the X-ray detector.
Figure 4:
FIG. 4 is the sectional three dimensional view of the partial scintillator screen in the X-ray detector.
Figure 5:
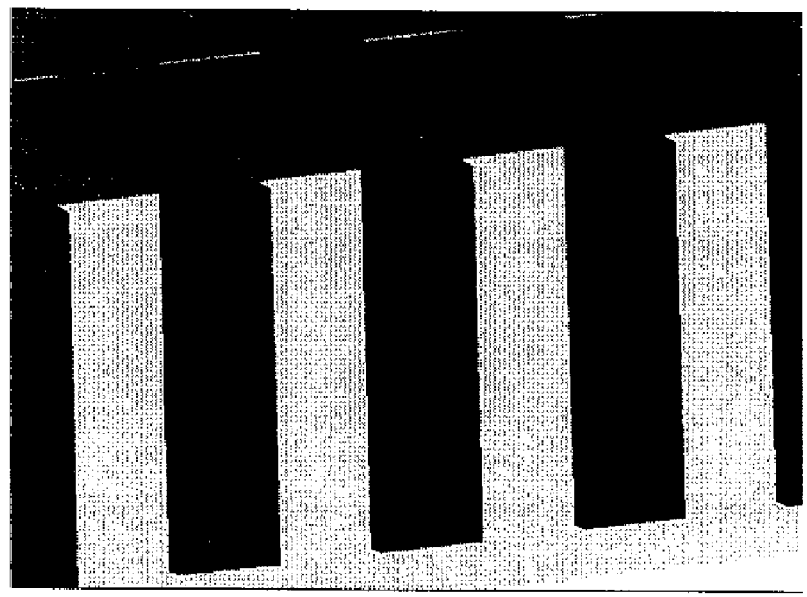
FIG. 5 is the schematic diagram of FIG. 4 after filling with X-ray sensitive material.
Figure 6:
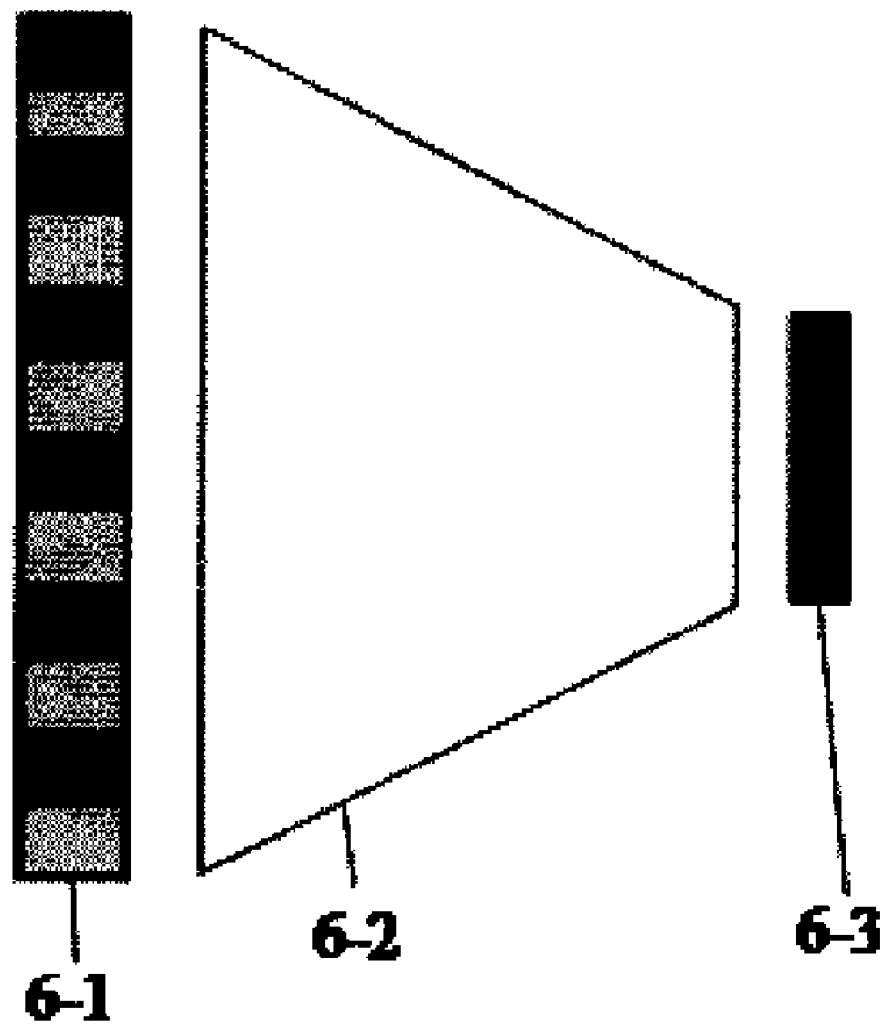
FIG. 6 is the structure schematic diagram for an X-ray detector using techniques of optical fiber taper coupling.

As shown in FIG. 1, in accordance with the direction of X-ray propagation, the basic components of present system include 1-1 X-ray tube, 1-2 filter, 1-3 object platform, 1-4 X-ray phase grating, 1-5 detector. System administration software and computer control the system. The key factors are: 1) The coherent X-ray beam from source array whose focal spots are linearly parallel arranged, has high energy and wide angle of de angle of divergence with 30-50 degree 2) The novel X-ray detector adopted in present invention plays dual roles of conventional analyzer grating and conventional detector. The basic structure of the detector includes a set of parallel array of X-ray scintillator screen, optical coupling system, area array detector or photoconductive X-ray detector. The structure and size of the X-ray scintillator screen and the photoconductive X-ray detector are consistent with the parallel-arranged linear X-ray beam with good coherence and high energy.

The novel X-ray tube described above is capable of generating an X-ray beam with good spatial coherence, high radiation flux, and wider emitting angles. A novel concept of parallel-arranged linear array of X ray emitter has been proposed by present inventor. According to the concept above, the X-ray emitter is a parallel-arranged linear array consisting of many line emitters, which are considered as independent coherent sources. Proper ranges of the width and length of each line are 50-100 μm and 0.3-2 mm, and preferable are 10-20 μm and 0.6-1.2 mm respectively. The duty ratio of the parallel-arranged linear array of the X-ray emitter is 10-50%, the optimal ratio is 20-25%. In contrast to the distance of object and source, the length of each line emitter is so small to insure the coherence of X-ray beam with shape of taper. Each cone of x-ray beam is individually coherent, but mutually incoherent. The invention of the novel X-ray tube lays the foundation for implementing the present differential phase-contrast X-ray imaging system. See CN patent 200610062487.1

The novel X-ray tube described above can work with continuous or pulse mode. By controlling the grid electrode located between the electronic or ionic emitter and the structured anode, the X-ray tube provides continuous or impulsive X-ray output.

Basic components of the novel X-ray detector described above include: 6-1 scintillator screen, 6-2 light coupling system, 6-3 area array CCD or CMOS detector. The periodic structural parameters of the parallel line in the parallel-arranged linear array of X-ray scintillator screen are determined by diffraction theory. The loop cycle of the X-ray detector includes a banded sensitive area and a banded insensitive area. When being perpendicular to the periodic structure, the whole insensitive band, which is composed with non-fluorescent material, is insensitive to the incident X-ray. In the same direction, the whole sensitive band is divided into a rectangular array of pixels filled by x-ray fluorescent material, so every pixel is highly sensitive to the incident X-ray. The aggregate width of sensitive band and insensitive band is exactly same as the periodicity of the X-ray interference pattern.

The area array detector of the X-ray detector described above is a photoconductive X-ray detector. The photoconductive detector is composed of independent unit made by X-ray photoconductive material. Multiple photoconductive units, which have the same structure parameters of the X-ray scintillator screen described above, are conformed together to generate an array structure.

The period ($P_2$) of the array X-ray scintillator screen or X-ray arrayed photoconductive detector should meet the relational equation: $P_2=0.5P_1(L+d_n)/L$. $P_1$ represents the period of phase grating, L represents the distance from X-ray source to phase grating, $d_n$ represents fractional Talbot imaging distance. Additional or optionally, the width of each independent pixel area "b" is no bigger than the one half of the period pitch ($P_2$). Length "a" is 0.5-10 times of period $P_2$.

Several materials, such as semi-conductive material like silicon, germanium, or metal material like aluminum, or stainless steel, or glass can be selected as the non-fluorescent material described above. The pixel area that is separated by non-fluorescent material is filled with fluorescent material like CsI:Tl, CsI:Na or $Gd_2O_2S$:Tb that emit visible or infrared light.

The light coupling system described above can be made of optical fiber taper, optical fiber panel, the combination of optical fiber taper and optical fiber panel, or optical lens.

The photoconductive material is non-crystal selenium, mercury iodide, or lead iodide. By using focused laser beam or focusing line laser beam, the pixel signal generated by the photoconductive material is readout dot by dot or line by line. The bases structure of the X-ray detector described above with dual functions of analyzer grating and detector is composed of 2-1 glass base, 2-2 dielectric material, 2-3 the transparent electrode, 2-4 photon conductive material, 2-5 electrode, wherein the photoconductive material is composed of non-crystal selenium, mercury iodide, or lead iodide. The "T" indicates the width of transparent electrode of 2-3. The integrated width of 2-2 and 2-3 is equal to period length P of the grating inference fringes. By using the focus point laser beam or the focus line laser beam, the signal of photoconductive material is readout dot by dot or line by line.

The energy of X-ray coming from the X-ray tube adopted in present system changes from 50 to 120 keV. By changing the thickness of the phase grating made of silicon, aluminum, or other material, the corresponding photon energy of the central wavelength can be controlled in a range of 7-100 keV. The bandwidth of incident X-ray is allowed in the order of ±20% around designed center energy. The filter described above is made of molybdenum, tungsten, aluminum, or other material. The central wavelength and bandwidth of X-ray beam downstream of the filter will match the thickness of the phase grating. A controlling mechanism is designed to align exquisitely the position of the above described X-ray emitter, filter, object plate, phase grating, and X-ray detector along the coaxial or axial direction.

A precise adjusting mechanism is designed to align exquisitely the above described X-ray source, phase grating, and array X-ray scintillator screen or photoconductive X-ray detector. By using the mechanism, the orientations of the parallel linear X-ray beam from the X-ray source, the direction of the phase grating line, and the one dimensional periodic structure of the X-ray array scintillator screen or photoconductive X-ray detector can be adjusted finely. In the perpendicular orientation of X-ray scintillator screen or photoconductive X-ray detector, the phase grating can also be adjusted.

The scintillator screen structure of the first X-ray detector provided in present invention is designed as an array structure with one-dimensional period. The loop cycle includes banded sensitive and insensitive areas that are sensitive and insensitive to X-ray, respectively. In the direction of perpendicular to the periodic structure, the whole area of the insensitive band is insensitive to the incident X-ray, and the whole area of the sensitive band is divided into many pixels, every pixel is highly sensitive to the incident X-ray. In one period of scintillator screen, the integrated width of sensitive band and insensitive band is exactly same as the periodicity of the X-ray interference pattern. The non-fluorescent material in the scintillator screen is semi-conductive material like silicon, germanium, or metal material like aluminum, or stainless steel, or glass. Array holes on the substrate are generated by etching methods like reactive ion etching, wet etching, photo-assisted electrochemical etching, or inductive coupling plasma reactive ion etching. The depth of the holes is usually 10-500 μm, and corresponds to the X-ray spectrum and the fluorescence material used. The array holes are filled with X-ray fluorescent material, which can emits visible or infrared light when being radiated by X-ray. When a larger scintillator screen is necessary, multiple optical fiber tapers can be used to couple images of scintillator on the area array of CCD or CMOS detector.

This system can be used in several fields like medical examination, non-destructive inspection, and other fields. The above description is only one of the preferred embodiments of the X-ray linear array of emitter, the X-ray detector with features of one dimensional spatial periodic structure, and these critical components are basis of X-ray differential interference contrast imaging system. X-ray source is not limited to X-ray tube using electron beam. When X-ray tube using ion beam is selected, except the ion source, other components are similar. It should be pointed out that the forms of the basic concept and basic methods of the present invention can be deduced.

The invention claimed is:

1. A differential interference phase-contrast X-ray imaging system comprising: an X-ray tube comprising parallel arrayed linear X-ray emitters with emission angle of 30-50 degree, which can generate a coherent hard X-ray; an X-ray filter; an object platform; an X-ray phase grating; an X-ray detector with the functions of detection and analysis including parallel arrayed X-ray scintillator screen, light coupling system and visible light area detector or parallel arrayed photoconductive x-ray detector, wherein the X-ray scintillator screen has one dimensional periodicity configured to detect the interferogram of the x-ray phase grating, wherein the X-ray scintillator screen has a periodic structure consisting of a banded X-ray sensitive area and a banded X-ray insensitive area in one periodicity, wherein the insensitive band is perpendicular to the periodic structure is made of material insensitive to X-rays, and the sensitive hand filled by fluorescent material of incident X-ray is divided into rectangle array of pixels by X-ray insensitive material in the direction—perpendicular to the periodic structure, wherein the insensitive material including semiconducting material of silicon, germanium or aluminous metal, stainless steel or glass, and the pixel area is filled with fluorescent material selected from the group consisting of CsI:Tl, CsI:Na or $Gd_2O_2S$:Tb which can emit visible light or near infrared wave when excited by X-ray.

2. A differential interference phase-contrast X-ray imaging system comprising: an X-ray tube comprising parallel arrayed linear X-ray emitters with emission angle of 30-50 degree, which can generate a coherent hard X-ray; an X-ray filter; an object platform; an X-ray phase grating; an X-ray detector with the functions of detection and analysis including parallel arrayed X-ray scintillator screen, light coupling system and visible light area detector or parallel arrayed photoconductive x-ray detector, wherein the X-ray scintillator screen has one dimensional periodicity configured to detect the interferogram of the x-ray phase grating, wherein the X-ray scintillator screen has a periodic structure consisting of a banded X-ray sensitive area and a banded X-ray insensitive area in one periodicity, wherein the insensitive band is perpendicular to the periodic structure is made of material insensitive to X-rays, and the sensitive band filled by fluorescent material of incident X-ray is divided into rectangle array of pixels by X-ray insensitive material in the direction—perpendicular to the periodic structure, wherein the visible light coupling system consists of optical fiber taper, optical fiber plate or optical lens or composite of optical fiber taper, optical fiber plate.

* * * * *